United States Patent
Axelson et al.

(10) Patent No.: US 11,857,422 B2
(45) Date of Patent: Jan. 2, 2024

(54) ACETABULAR CUP SYSTEM

(71) Applicant: Encore Medical, LP, Austin, TX (US)

(72) Inventors: Stuart L. Axelson, Succasunna, NJ (US); Adam Shallenberg, Cedar Park, TX (US); Kevin Wills, Cedar Park, TX (US); David Link, Austin, TX (US)

(73) Assignee: Encore Medical, LP, Austin, TX (US)

( * ) Notice: Subject to any disclaimer, the term of this patent is extended or adjusted under 35 U.S.C. 154(b) by 401 days.

(21) Appl. No.: 17/166,665

(22) Filed: Feb. 3, 2021

(65) Prior Publication Data

US 2021/0236290 A1    Aug. 5, 2021

Related U.S. Application Data

(60) Provisional application No. 62/970,044, filed on Feb. 4, 2020.

(51) Int. Cl.
*A61F 2/34*     (2006.01)
*A61F 2/30*     (2006.01)

(52) U.S. Cl.
CPC ...... *A61F 2/34* (2013.01); *A61F 2002/30092* (2013.01); *A61F 2002/30156* (2013.01); *A61F 2002/30383* (2013.01); *A61F 2002/30784* (2013.01); *A61F 2002/3403* (2013.01); *A61F 2002/349* (2013.01); *A61F 2002/3414* (2013.01); *A61F 2310/00017* (2013.01); *A61F 2310/00029* (2013.01); *A61F 2310/00131* (2013.01)

(58) Field of Classification Search
CPC ............... A61F 2002/30383; A61F 2002/3414
See application file for complete search history.

(56) References Cited

U.S. PATENT DOCUMENTS 4,681,589 A    7/1987   Tronzo
5,021,062 A    6/1991   Adrey et al.
(Continued)

FOREIGN PATENT DOCUMENTS

CN    209075035 U    7/2019
EP    1308141 A1    5/2003
(Continued)

OTHER PUBLICATIONS

International Search Report dated May 11, 2021 cited in PCT/US2021/016411.

*Primary Examiner* — Brian A Dukert
(74) *Attorney, Agent, or Firm* — Veros Legal Solutions, LLP

(57) ABSTRACT

An acetabular cup assembly for use with liners is described. The acetabular cup assembly includes a cup and a liner. The cup has an outer surface, a generally concave inner surface and a top face. The inner surface includes a cylindrical band having a plurality of inward-facing recessed scallops, a tapered wall adjacent to the band, and an inner spherical surface adjacent the tapered wall. The inner spherical surface has a substantially uniform radius of curvature. A single groove interrupts the spherical surface. The liner has a substantially convex outer surface and includes a rim and a plurality of outward-projecting scallops adjacent the rim. The scallops of the liner are configured to engage the scallops of the cup when the liner is seated in the cup. Related methods of use are also provided.

36 Claims, 9 Drawing Sheets

(56) References Cited

U.S. PATENT DOCUMENTS

| | | | |
|---|---|---|---|
| 5,133,764 | A | 7/1992 | Pappas et al. |
| 6,152,961 | A | 11/2000 | Ostiguy, Jr. et al. |
| 6,475,243 | B1 | 11/2002 | Sheldon et al. |
| 7,169,185 | B2 | 1/2007 | Sidebotham |
| 7,326,253 | B2 | 2/2008 | Synder et al. |
| 8,066,778 | B2 | 11/2011 | Meridew et al. |
| 8,123,815 | B2 | 2/2012 | Meridew et al. |
| 8,585,769 | B2 | 11/2013 | Vankoski et al. |
| 8,679,187 | B2 | 3/2014 | Allen et al. |
| 8,801,798 | B1 * | 8/2014 | Smith ........................ A61F 2/34 623/22.24 |
| 9,144,497 | B2 * | 9/2015 | Sun ........................ A61F 2/34 |
| 9,463,094 | B2 | 10/2016 | Allen et al. |
| 10,307,255 | B1 * | 6/2019 | Hutton ................... A61F 2/4609 |
| 10,383,745 | B2 | 8/2019 | Allen et al. |
| 2007/0106392 | A1 | 5/2007 | Servidio et al. |
| 2014/0228966 | A1 | 8/2014 | Smith |
| 2017/0020688 | A1 | 1/2017 | Allen et al. |
| 2019/0159902 | A1 | 5/2019 | Hutton et al. |

FOREIGN PATENT DOCUMENTS

| | | |
|---|---|---|
| EP | 3285691 A1 | 2/2018 |
| WO | 2011008757 A1 | 1/2011 |

\* cited by examiner

ACETABULAR CUP SYSTEM

CROSS-REFERENCE TO RELATED APPLICATIONS

This application claims priority to U.S. Provisional Application No. 62/970,044, filed on Feb. 4, 2020, the entire contents of which is hereby incorporated by reference.

FIELD OF THE INVENTION

The present invention relates to acetabular cups and bearings and more particularly, to acetabular cup assemblies for use in connection with hip replacement devices and methods.

BACKGROUND

Hip arthroplasty or replacement refers to a surgical procedure in which the hip joint is replaced by a prosthetic implant. Total hip arthroplasty has been used since the 1960s for the treatment of destructed hip joints and replaces both the femoral component and the acetabular surface of the joint. Artificial hip joints are generally ball and socket joints, designed to match as closely as possible to the natural joint function. Generally, the artificial socket is implanted in the acetabulum bone, and the artificial ball articulates in the socket. A stem structure attached to the ball is implanted in the patient's femoral bone, thereby securing the ball in position. In total hip replacement surgery, a patient's natural hip is replaced by an acetabular cup component that replaces the acetabular socket, and a femoral component, or the stem-and-ball component, which replaces the femoral head.

Total hip arthroplasty (THA) is considered one of the most successful surgical procedures providing pain relief and improvement of function in patients with end-stage hip arthritis that is non-responsive to non-operative treatments. As health care continues to improve and life expectancy increases, the demand for total joint replacement will grow to reflect this more active, aging population. The number of THAs performed in the United States is projected to reach 572,000 by 2030, an increase of 174% compared to 2005.

Reducing or preventing medical and mechanical complications such as post-operative THA instability is of the utmost importance. The incidence of instability after THA in the primary and revision setting has been reported as high as 7% and 25%, respectively. Risk factors for instability after THA are multifactorial and may be patient-specific (gender, age, abductor deficiency) or related to operative variables (surgical approach, component malposition, femoral head diameter). Instability after THA remains one of the major causes of readmission and revision surgery accounting for 32.4% of THA readmissions and 22.5% of all THA revisions in the United States.

With total hip replacement, the femoral head and the surface of the acetabulum are replaced with prosthetic devices. In order to install the acetabular cup, the surgeon prepares the bone by reaming the acetabular socket to create a surface for accepting a cup. The cup may be held in place by bone cement, an interference or press fit, or bone screw. The new acetabular cup is implanted securely within the prepared hemispherical socket. The inner portion of the implant is placed within the metal cup and fixed into place. Then, the femur is prepared to receive the stem. The proximal end of the femur is at least partially resected to expose the central portion of the bone. Generally, at least part of the greater femoral trochanter is resected to gain access to the central portion of the femur, specifically, the medullary canal. In the central portion, a cavity is created that matches the shape of the implant stem, utilizing the existing medullary canal. The top end of the femur may be planed and smoothed. If the ball is a separate piece, the proper size is selected and attached. Finally, the ball is seated within the cup so that the joint is properly aligned, and the incision is closed.

One of the challenges faced with total hip replacement procedures is achieving a secure attachment between the femoral implant and the acetabular cup component and the patient's bone. Conventional acetabular cup devices are typically hemispherical cups which are secured within a prepared acetabulum. Acetabular systems have been developed which include an acetabular cup and a bearing or liner. Acetabular cups generally include a tapered inside geometry and locking groove in which a tapered hard or soft bearing can be inserted.

In hip arthroplasty, a variety of bearing materials are available for the cup portion of the implant and the selection of a particular bearing material may be determined by the surgeon before or even during surgery. Depending upon the patient needs, the bearings/liners can be constructed from polyethylene or a biocompatible metal. As described in US Patent Publication No, 2017/0020688, it may be advantageous to utilize an acetabular cup that accepts multiple bearing liners so that a surgeon may select an appropriate liner to optimize fit and/or address patient needs. An acetabular cup assembly for use with multiple bearings has value both from a manufacturing perspective (inasmuch as only one cup is required for multiple applications) and from the perspective of a surgeon as it offers greater flexibility to make adjustments to the hip prothesis and may reduce the overall operation time.

There is a need for acetabular systems which reduce micromotion between a liner and the cup. Further, it would be a boon to hip arthroplasty for an acetabular cup assembly which provides an enhanced fit and greater flexibility for the surgeon to make adjustments to the hip prosthesis.

It should be noted that this Background is not intended to be an aid in determining the scope of the claimed subject matter nor be viewed as limiting the claimed subject matter to implementations that solve any or all of the disadvantages or problems presented above. The discussion of any technology, documents, or references in this Background section should not be interpreted as an admission that the material described is prior art to any of the subject matter claimed herein.

SUMMARY

In one implementation, an acetabular cup system is provided. The system includes a cup configured to receive a plurality of liners. The cup includes an outer surface configured to engage an anatomy. The cup includes a generally concave inner surface. The cup includes a top face at an upper end of the cup. The inner surface includes a cylindrical band having disposed therein a plurality of inward-facing recessed scallops adjacent to the top face. The inner surface includes a tapered wall disposed adjacent to the cylindrical band. The inner surface includes an inner spherical surface adjacent to the tapered wall, the inner spherical surface having a substantially uniform radius of curvature and with a single groove interrupting the spherical surface. The system includes a liner having a substantially convex outer surface configured to be received within the concave inner surface of the cup. The liner includes a rim and a plurality of outward-projecting scallops adjacent to the rim. When the liner is seated in the cup, each of the outward-projecting scallops of the liner are configured to engage with a respective one of the inward-facing recessed scallops of the cup.

In another implementation, a method of using an acetabular cup system is provided. The method includes preparing a bone of a patient for receiving a cup of the acetabular cup system. The method includes securing the cup to the prepared bone of the patient. The cup includes an outer surface configured to engage an anatomy, a top face at an upper end of the cup, and a generally concave inner surface. The generally concave inner surface includes a cylindrical band having disposed therein a plurality of inward-facing recessed scallops adjacent to the top face, a tapered wall disposed adjacent to the cylindrical band, and an inner spherical surface adjacent to the tapered wall, the inner spherical surface having a substantially uniform radius of curvature and a single groove interrupting the spherical surface. The method includes aligning a liner over the cup. The liner includes a substantially convex outer surface configured to be received within the concave inner surface of the cup, a rim, and a plurality of outward-projecting scallops adjacent to the rim. The method includes securing the liner within the cup such that each of the outward-projecting scallops of the liner engage with a respective one of the inward-facing recessed scallops of the cup.

It is understood that various configurations of the subject technology will become apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

Various embodiments are discussed in detail in conjunction with the Figures described below, with an emphasis on highlighting the advantageous features. These embodiments are for illustrative purposes only and any scale that may be illustrated therein does not limit the scope of the technology disclosed. These drawings include the following figures, in which like numerals indicate like parts.

DETAILED DESCRIPTION

Figure 1:
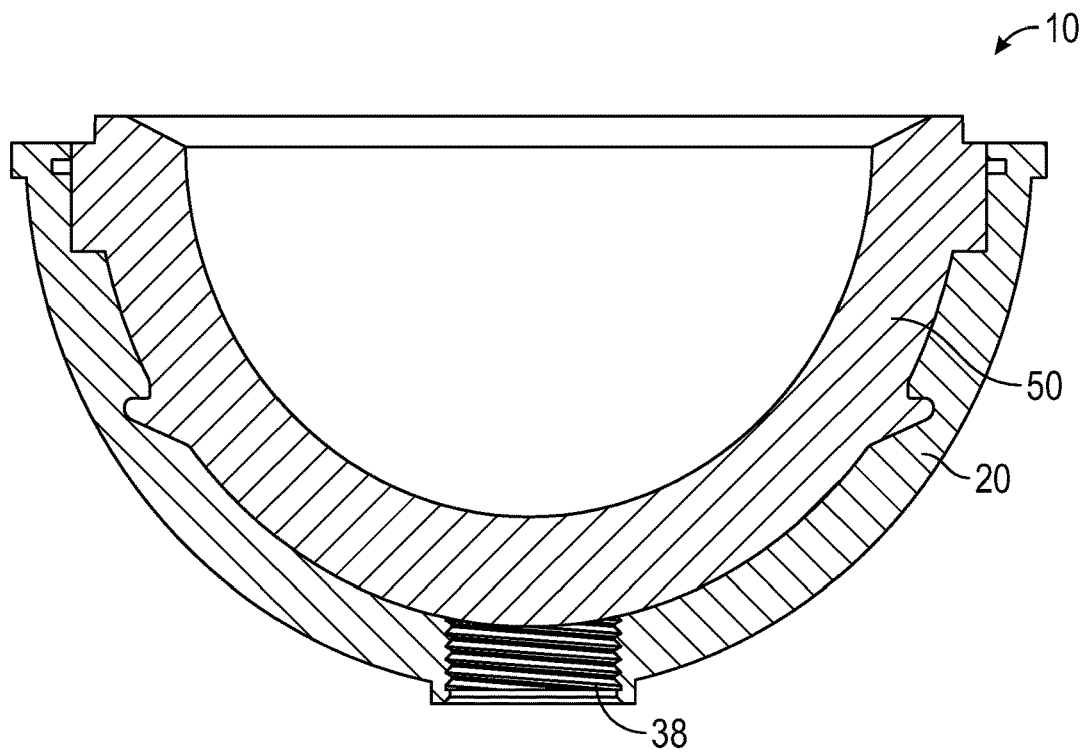
FIG. 1 cross sectional view of an acetabular cup assembly having a cup and a liner, according to some embodiments.

The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

Implementations of the technology described herein are directed generally to an acetabular cup assembly comprising a cup and a liner.

General Interpretive Principles for the Present Disclosure

Various aspects of the novel systems, apparatuses, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

With respect to the use of plural vs. singular terms herein, those having skill in the art can translate from the plural to the singular and/or from the singular to the plural as is appropriate to the context and/or application. The various singular/plural permutations may be expressly set forth herein for sake of clarity.

When describing an absolute value of a characteristic or property of a thing or act described herein, the terms "substantial," "substantially," "essentially," "approximately," and/or other terms or phrases of degree may be used without the specific recitation of a numerical range. When applied to a characteristic or property of a thing or act described herein, these terms refer to a range of the characteristic or property that is consistent with providing a desired function associated with that characteristic or property.

In those cases where a single numerical value is given for a characteristic or property, it is intended to be interpreted as at least covering deviations of that value within one significant digit of the numerical value given.

If a numerical value or range of numerical values is provided to define a characteristic or property of a thing or act described herein, whether or not the value or range is qualified with a term of degree, a specific method of measuring the characteristic or property may be defined herein as well. In the event no specific method of measuring the characteristic or property is defined herein, and there are different generally accepted methods of measurement for the characteristic or property, then the measurement method should be interpreted as the method of measurement that would most likely be adopted by one of ordinary skill in the art given the description and context of the characteristic or property. In the further event there is more than one method of measurement that is equally likely to be adopted by one of ordinary skill in the art to measure the characteristic or property, the value or range of values should be interpreted as being met regardless of which method of measurement is chosen.

It will be understood by those within the art that terms used herein, and especially in the appended claims (e.g., bodies of the appended claims) are intended as "open" terms unless specifically indicated otherwise (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C" is used, such a construction would include systems that have A alone, B alone, C alone, A and B together without C, A and C together without B, B and C together without A, as well as A, B, and C together. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include A without B, B without A, as well as A and B together."

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Any methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Disclosure of Several Example Embodiments

Turning now to the figures, FIG. 1 illustrates an acetabular cup assembly 10. The assembly 10 includes an acetabular cup 20 and an acetabular liner 50. The cup 20 is adapted for use with the liner 50 as will be described in greater detail below with reference at least to FIGS. 2-13. As best seen in FIG. 3, the cup 20 comprises an inner surface 14 and an outer surface 16. The outer surface 16 is generally hemispherical in shape and is configured to create a press fit with prepared acetabulum bone of a pelvis. The outer surface 16 can include a porous coating configured to provide an improved matrix for mineralization and promote bone in-growth into the cup 20. The porous coating may cover all or only a portion of the outer surface 16 of the cup 20. The cup 20 can be constructed of a biocompatible metal or other suitable material such as a ceramic material. Suitable metals include, without limitation, stainless steel, titanium, titanium alloy, cobalt chromium molybdenum, cobalt chromium, or other biocompatible material.

In some embodiments, the cup 20 comprises one or more fixation holes 40 configured to receive a fixation device such as a screw or peg to attach the cup 20 to prepared acetabulum (see, e.g., FIG. 3). The fixation hole(s) 40 can generally be used for passing a screw or other fixation member into the acetabular portion during implantation and fixation of the acetabular cup 20. It will be appreciated that a plurality of fixation holes can be provided at various positions on the cup 20 and a clinician or practitioner can selectively pass screws for fixing the cup 20 to the acetabulum of the patient. Additional fixation means can be employed to fix the cup 20 to the pelvis, including, without limitation, modular pegs, projections, spikes, or porous coating of the outer surface of the cup 20 as described anywhere in this disclosure.

Figure 10:
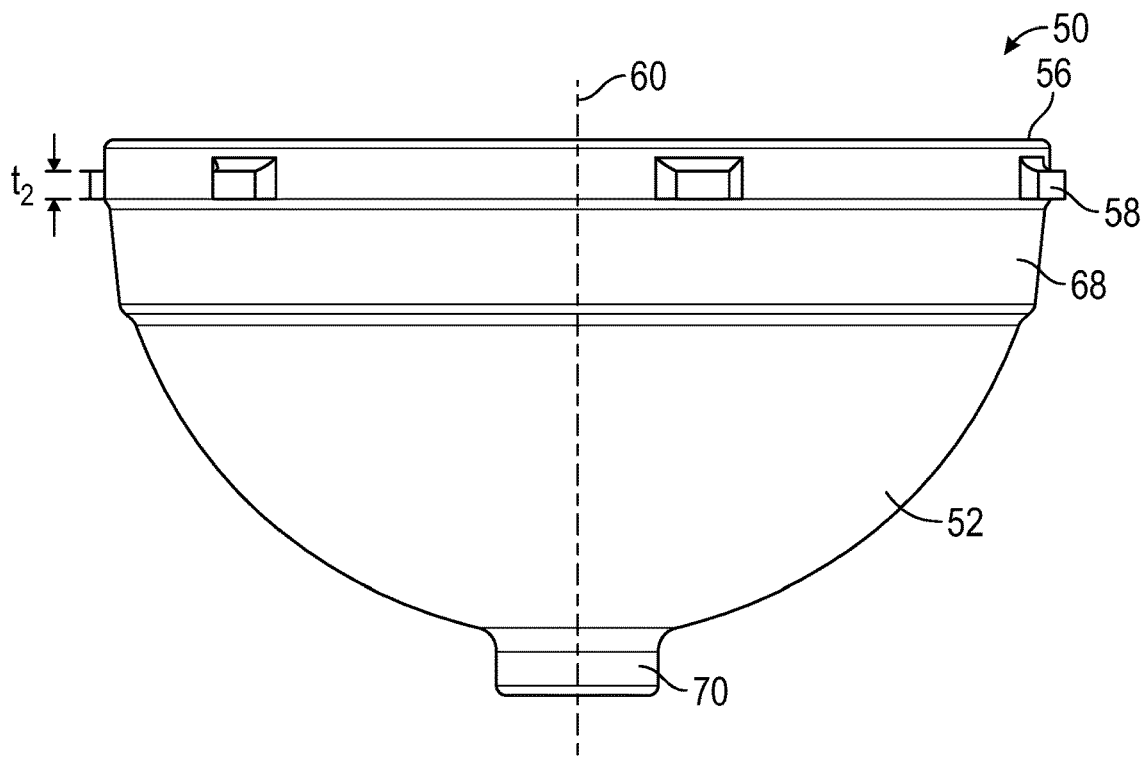
FIG. 10 illustrates a side view of a liner, according to some embodiments.
Figure 12:
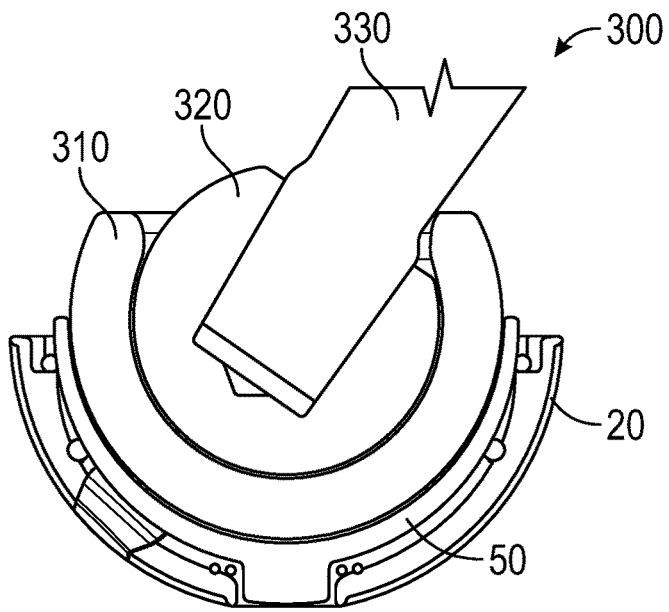
FIG. 12 illustrates an acetabular cup assembly having a cup, a liner, and a femoral assembly according to some embodiments.

In some embodiments, cup 20 further comprises an aperture or hole 38 configured, in some embodiments, to receive a mating peg 70 of a liner 50 (see, e.g., FIGS. 10 and 12). As illustrated at least in FIG. 1, the aperture 38 may be threaded to receive and engage with such a mating peg 70 of liner 50. In one embodiment, the aperture 38 is located at an apex (e.g., a polar base) of the cup 20 as is illustrated in at least FIGS. 1 and 3. However, it will be appreciated that the cup 20 can optionally include additional apertures at other locations for the purpose of inserting the cup 20 into a prepared acetabulum, receiving an insertion tool, and/or receiving and/or securing the liner 50 within the cup 20.

Figure 2:
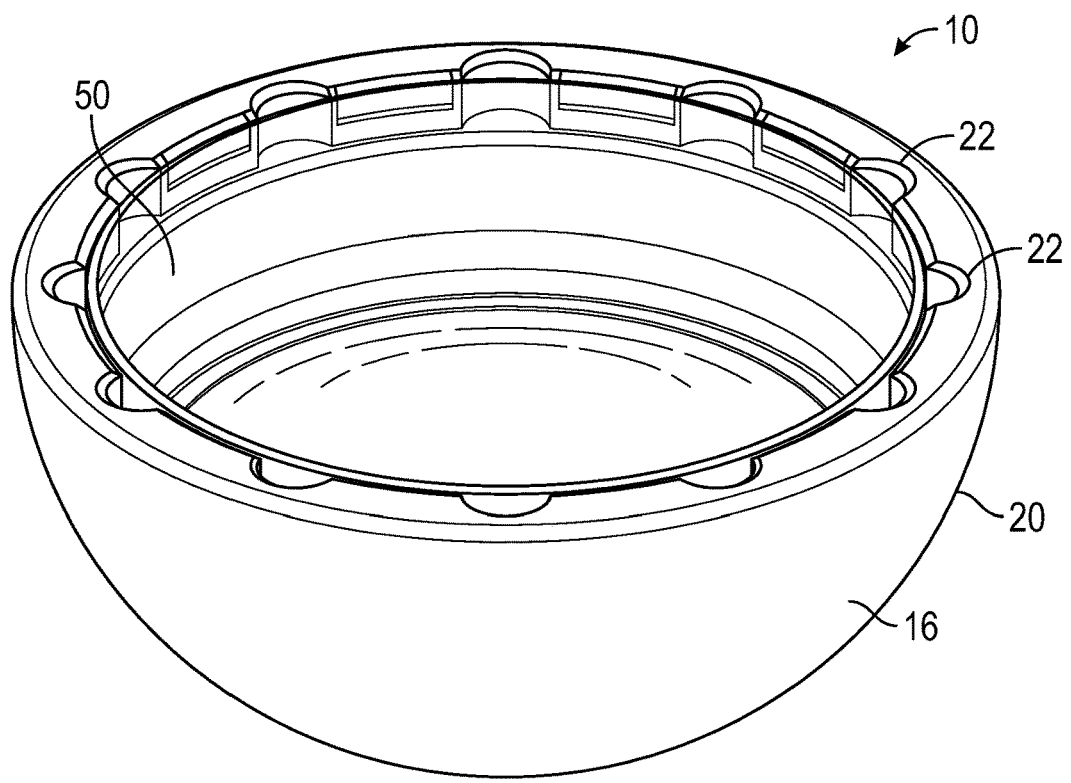
FIG. 2 is a top perspective view of an acetabular cup and a liner, according to some embodiments.
Figure 3:
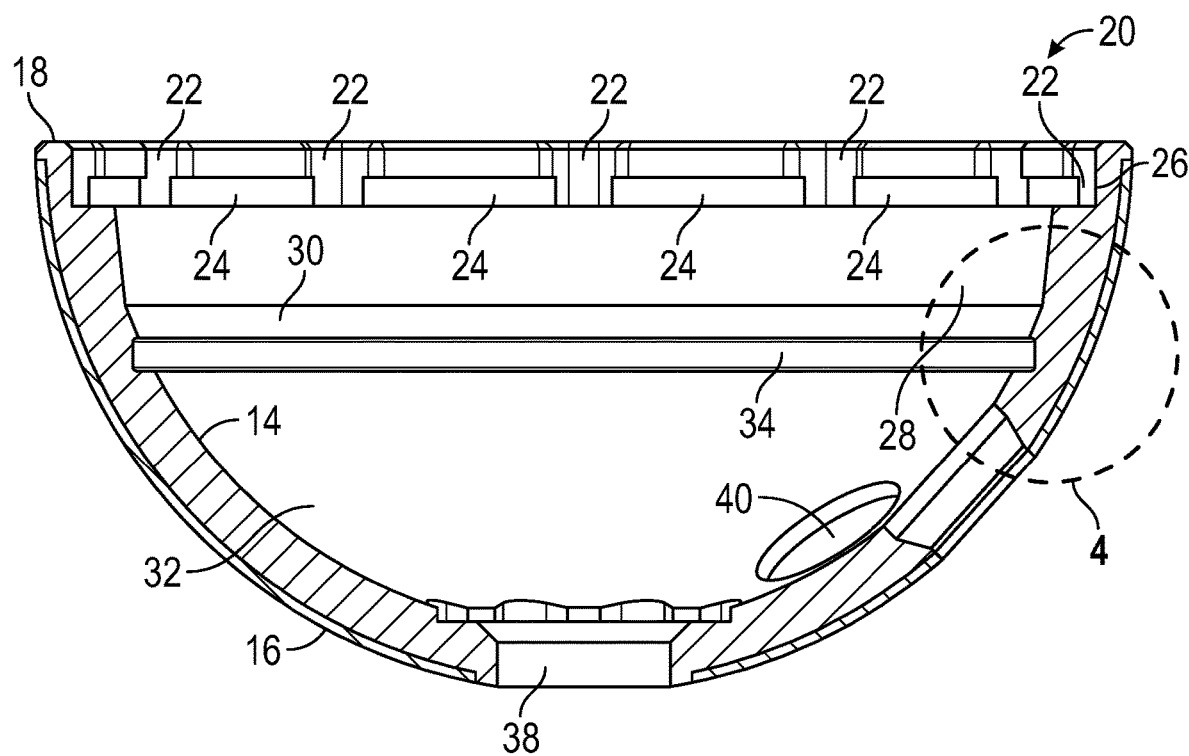
FIG. 3 is a cross-sectional view of an acetabular cup, according to some embodiments.
Figure 4:
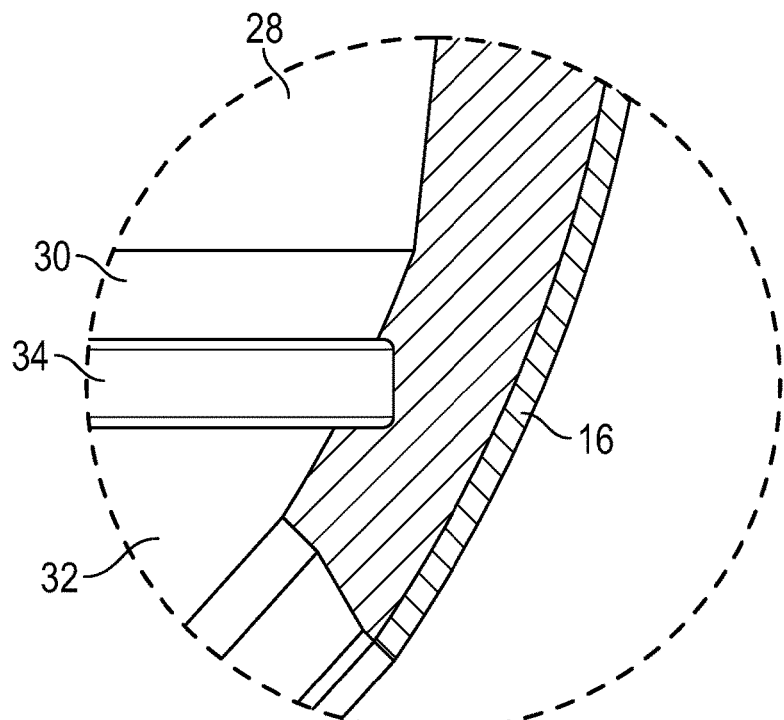
FIG. 4 is an enlarged cross-sectional view of a portion of the acetabular cup of FIG. 3, according to some embodiments.

As best seen in FIGS. 1-3, the inner surface 14 of the cup 20 comprises a generally concave shape. Nevertheless, it will be appreciated that other shapes may be employed. The inner surface 14 is designed to accept and lock a liner 50 (also called a bearing herein). In some embodiments, liner 50 can comprise polyethylene (e.g., a "poly") liner or bearing, in some embodiments, having a liner locking feature and, in some embodiments, for use in a standard mobility articulation, as will be described in greater detail below with reference to at least FIGS. 6-9. In some embodiments, the liner 50 can comprise a metal and/or metal alloy liner or bearing for a dual mobility articulation, as will be described in greater detail below with reference to at least FIGS. 10-12.

The cup 20 comprises an annular cylindrical band 26 formed at an upper end of the cup 20. The annular cylindrical band 26 has a flat top face 18. An inner surface of the annular cylindrical band 26 may be inset or recessed (e.g., radially inset and/or recessed) from an adjacent lower portion of the inner surface 14, thereby allowing for engagement of the liner 50.

A plurality of inward-facing recessed scallops 22 are disposed on the inner surface of the annular cylindrical band 26 and adjacent the top face 18. The inward-facing recessed scallops 22 are configured to receive and accept mating outward-protruding scallops 58 on the liner 50 and, thereby, achieve and/or provide anti-rotational stability between the liner 50 and the cup 20. In some embodiments, the plurality of inward-facing recessed scallops 22 can be evenly spaced and/or distributed around annular cylindrical band 26. In some embodiments, the cup 20 includes at least 12 inward-facing recessed scallops 22. However, the present disclosure is not so limited and any number of inward-facing recessed scallops 22 are contemplated. Advantageously, in some embodiments, the cup 20 includes the same number of inward-facing recessed scallops 22 as there are corresponding outward-protruding scallops 58 on the liner 50. In some other embodiments, the cup 20 includes a greater number of inward-facing recessed scallops 22 (e.g., 12 inward-facing recessed scallops) than the liner 50 has outward-protruding scallops 58 (e.g., 6 outward-protruding scallops). In some embodiments, a number of evenly spaced inward-facing recessed scallops 22 of the cup 20 is an integer multiple of a number of evenly outward-protruding scallops 58 on the liner 50 to ensure multiple compatible rotational orientations between the cup 20 and the liner 50.

A combination of the cylindrical band 26 and the plurality of inward-facing recessed scallops 22 also affords advantages with respect to manufacture. More particularly, because the plurality of inward facing scallops 22 in the cup 20 project from the substantially vertically-oriented cylindrical band 26, instead of a tapered or substantially hemispherical surface, the mating outward-protruding scallops 58 on the liner 50 can be machined on a corresponding cylindrical band easily using standard lathe equipment.

Figure 5:
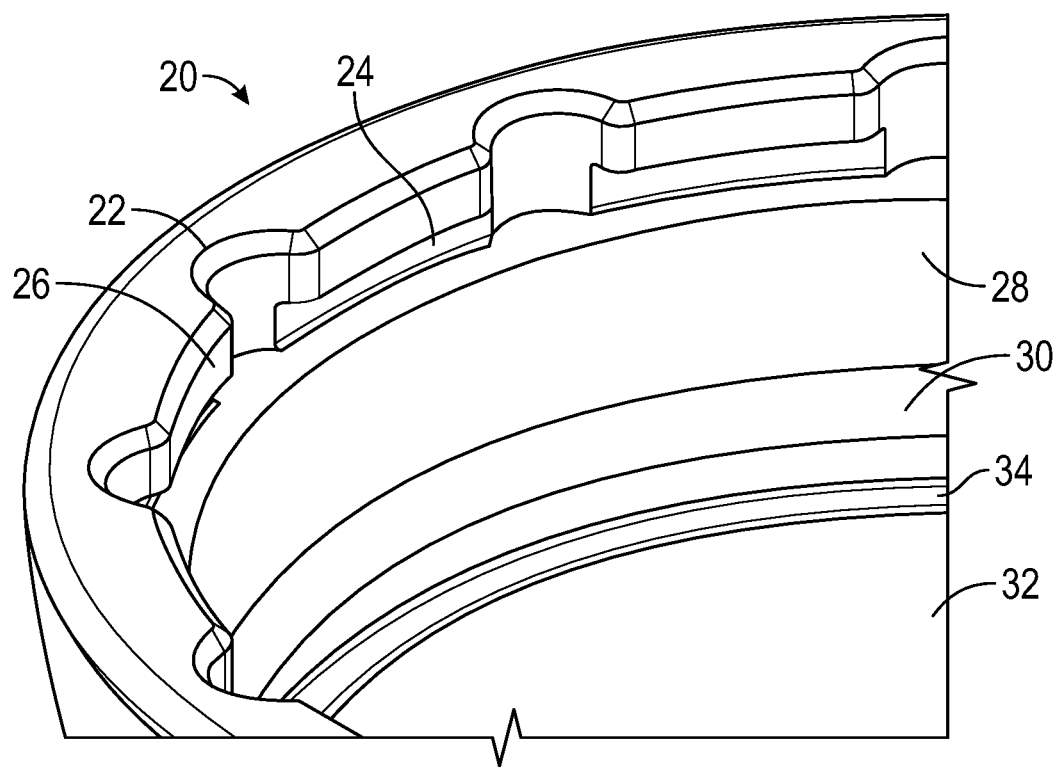
FIG. 5 is a top perspective view of a portion of the acetabular cup of FIG. 2, according to some embodiments.

In some embodiments, a lower portion of the annular cylindrical band 26 comprises an inward-facing recess or groove 24 (see, e.g., FIGS. 3 and 5). This recess or groove 24 may be configured for use with surgical instruments, such as trial liners or the like, but is not intended to affect or interact with the liner 50.

The cup 20 further includes an upper partially-tapered surface 28 extending immediately below cylindrical band 26 and towards a bottom of the cup 20. In some such embodiments, the taper of upper tapered wall portion 28 has a substantially semi-conical shape, rather than a substantially semi-hemispherical shape such that, for example, a cross-section of an inward-facing surface of upper tapered wall portion 28 (see, e.g., FIG. 3) follows a substantially straight line, rather than a curved or semi-circular line. In some embodiments, the tapered wall portion 28 creates an interference fit with the liner 50. In some embodiments, the upper tapered wall portion 28 can have a taper of between about 2 degrees and about 40 degrees from a vertical orientation when cup 20 is oriented as shown in FIG. 3. In some embodiment, the upper tapered wall portion 28 has a taper of between about 9 degrees and about 20 degrees. In some embodiments, the upper tapered wall portion 28 has taper of between about 10 degrees and about 15 degrees. In another aspect, the upper tapered wall portion 28 has taper of about 12 degrees. In some embodiments, the design of the acetabular cup 20 provides clearance for a poly liner with respect to the tapered wall portion 28.

Adjacent the base or bottom edge of the tapered wall portion 28, the cup 20 comprises an inner spherical surface 32. In some embodiments, an annular groove 34 is formed in the inner surface 14 of the cup 20 and intersects or interrupts the inner spherical surface 32 such that a top portion 30 of the inner spherical surface 32 is disposed above the annular groove 34 and the remainder of the inner spherical surface 32 is disposed below the annular groove 34. In some such embodiments, groove 34 extends peripherally or circumferentially about the inner spherical surface 32 of the cup 20 and defines a bottom edge of the top portion 30 of the inner spherical surface 32. In some embodiments, groove 34 has a substantially cylindrical shape, e.g., a sidewall of annular groove 34 has a substantially vertical orientation when the cup 20 is in the orientation shown in, e.g., FIGS. 3 and 4. In some embodiments, the groove 34 extends fully about the interior of the cup 20. In some other embodiments, the groove 34 may be discontinuously spaced within the interior of the cup 20, may have a "C" shape, a hemispherical shape, or some other suitable shape.

The sections of the inner spherical surface 32 above (30) and below (32) the groove 34 have a uniform radius of curvature. Accordingly, the groove 34 does not protrude beyond a base of the tapered wall portion 28 as can be seen at least in FIG. 4, which illustrates an enlarged cross-sectional view of the locking groove 34 as an interruption of the spherical inner surface 32 of the cup 20. In some, but not all embodiments, the groove 34 acts as a locking feature for a liner 50. In some such embodiments, the groove 34 is configured to capture a locking feature 62 of the liner 50 as will be discussed with reference to at least FIGS. 6-8D below.

Certain aspects of a liner 50 will now be described in connection with at least FIGS. 6-11 and in connection with at least FIGS. 10 and 11. As used herein, the terms "liner" and "bearing" are used interchangeably to refer to a body comprising a bearing material and that fits within the acetabular cup 20. In some embodiments, the liner 50 comprises polyethylene, e.g., a high molecular weight and/or cross-linked polyethylene. Alternatively, the liner 50 may be a metal bearing constructed from, e.g., stainless steel, titanium, titanium alloy, cobalt chromium molybdenum, cobalt chromium, a shape memory alloy such as nitinol, tantalum or other composites or biocompatible material(s). In yet another aspect, the liner 50 can be a ceramic liner made from, e.g., aluminum oxide, zirconium oxide, tetragonal zirconia polycrystal, alumina-zirconia composites, and/or non-oxide ceramics such as silicon carbide and silicon nitride.

In some embodiments, the liner 50 can be pre-assembled to the cup 20 prior to insertion into a patient. In some other embodiments, the cup 20 can be positioned in a patient first and then the liner 50 can be introduced and positioned within the cup 20. Thus, the acetabular system described herein contemplates at least a two-piece component design, which can be assembled prior to or during surgery.

Figure 6:
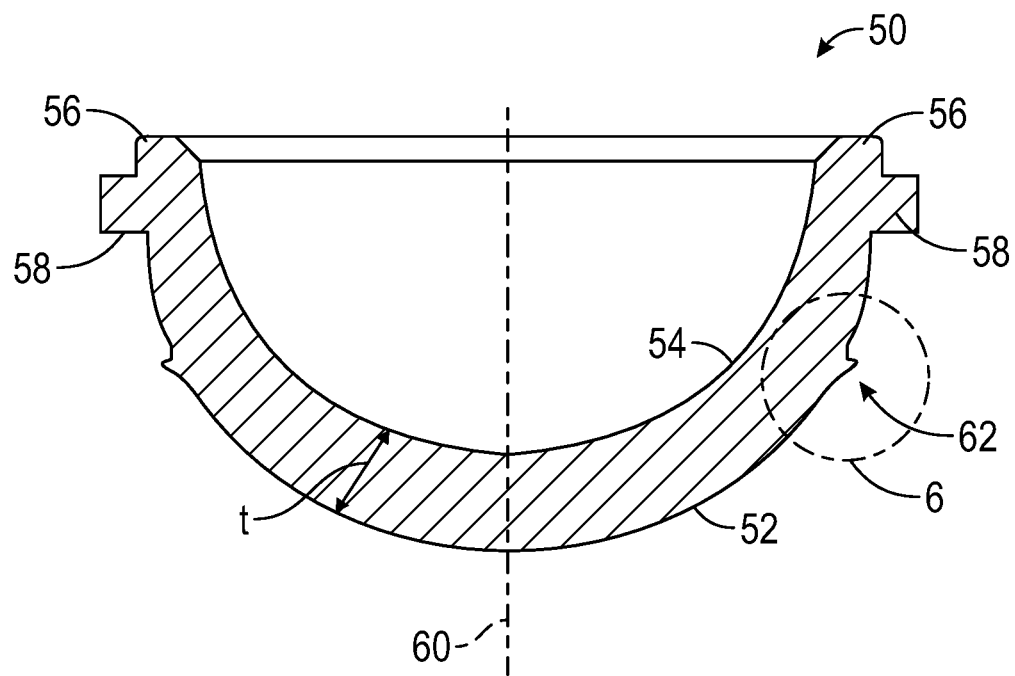
FIG. 6 is a cross-sectional view of a liner, according to some embodiments.

Turning to FIG. 6, in some embodiments, the liner 50 is symmetric about at least one plane coincident with central axis 60. However, once installed, rotation of the liner 50 within the cup 20 is prevented and micromotion therebetween is reduced at least partly as a result of interlocking of a plurality of outward-protruding scallops 58 on the liner 50 with the inward-facing protrusions 22 of the cup 20.

In some embodiments, the plurality of outward-protruding scallops 58 are evenly spaced and/or distributed around liner 50. As described above, in some embodiments, the liner 50 includes the same number of outward-protruding scallops 58 as the cup has inward-facing recessed scallops 22. In some other embodiments, the liner 50 includes a lesser number of outward-protruding scallops 58 (e.g., 6 outward-protruding scallops) than the cup 50 has inward-facing recessed scallops 22 (e.g., 12 inward-facing recessed scallops). And in some embodiments, a number of evenly spaced inward-facing recessed scallops 22 of the cup 20 is an integer multiple of a number of evenly outward-protruding scallops 58 on the liner 50 to ensure multiple compatible rotational orientations between the cup 20 and the liner 50.

In some embodiments, e.g., where the liner 50 is a poly liner, the liner 50 can have at least a portion with an increased thickness compared to conventional poly liners. A thicker poly liner rim offers numerous benefits. For example, a thicker poly liner reduces the likelihood of impingement damage failure, which, in turn, lessens the incidence of hip dislocation, which is a serious complication in total hip replacement. Thinner poly liners can lead to cracking at the rim or locking mechanism on the acetabular cup.

The liner 50 is designed to mate with the cup 20. Accordingly, similar to the cup 20, the liner 50 is substantially hemispherical in shape and has a liner outer surface 52, which is substantially convex (as viewed from the outside) and a liner inner surface 54, which is substantially concave (as viewed from the inside).

The liner 50 comprises a liner rim 56 disposed at the top of the liner outer surface 52. The liner 50 has a thickness t, measured between the liner outer surface 52 and the liner inner surface 54. In some embodiments, the thickness t of the liner 50 is substantially uniform. In some other embodiments, the thickness t of the liner 50 varies between the liner rim 56 and the liner apex (where axis 60 crosses the liner 50 cross-section at the bottom of FIG. 6).

The liner 50 comprises a plurality of outward-protruding scallops 58 which extend from the outer surface 52 of the liner 50 at the rim 56. As described above, these outward-protruding scallops 58 are configured to facilitate the alignment and fixation of the liner 50 with respect to the cup 20 by engaging the inward-facing recessed scallops 22 of the cup 20 and substantially rotationally fixing the liner 50 with respect to the cup 20. In one embodiment, the number of outward-protruding scallops 58 is equal to the number of inward-facing recessed scallops 22 of the cup 20. In another embodiment, the number of outward-protruding scallops 58 is less than the number of inward-facing scallops 22 of the cup 20. For example, in some embodiments, the number of outward-protruding scallops 58 may be half the number (e.g., 6) of inward-facing recessed scallops 22 of the cup 20 (e.g., 12).

In some embodiments, the liner outer surface 52 can also include a locking feature 62, for example as illustrated in FIGS. 6-9. The locking feature 62 can be formed by conventional molding and forming techniques and is configured to engage with the groove 34 within the inner spherical surface 32 of the cup 20 during implantation, positioning, and fixing of the liner 50 within the cup 20. The locking feature 62 is preferably integral with the liner 50. The locking feature 62 snaps into groove 34 to thereby secure the liner 50 in position relative to the cup 20. In some embodiments, the locking feature 62 is formed as a continuous overhang around the exterior of the liner 50. In some other embodiments, the locking feature 62 alternatively comprises a plurality of segmented projections having discreet projection regions around the exterior of the liner 50. In some embodiments, the locking feature 62 has a substantially angular (i.e. substantially non-rounded) geometry.

Figure 7:
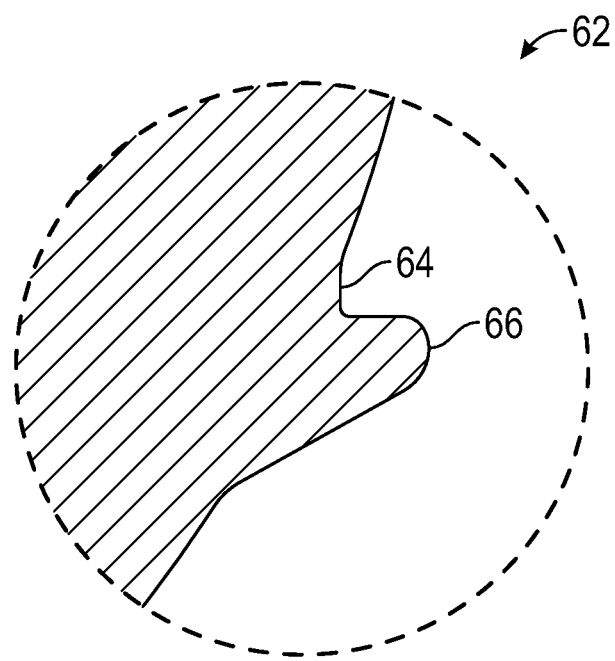
FIG. 7 is an enlarged cross-sectional view of a locking feature of the liner of FIG. 5, according to some embodiments.

In one embodiment, the locking feature 62 is substantially triangular in shape as best illustrated in the enlarged partial view of FIG. 7. It will be appreciated, however, that various geometries can be employed for the locking feature 62 such that the locking feature 62 is sufficiently captured as it engages with the groove 34. Notably, the locking feature 62 includes an angled portion 64 and an extension lip 66. In some embodiments, the angled portion 64 diverges from the hemispherical shape of the outer surface 52 of the liner 50 such that angled portion 64 has a substantially vertical orientation (e.g., substantially cylindrical face) when the liner 50 is oriented as shown in FIG. 6. The extension lip 66 extends from the angled portion 64. Preferably, the extension lip 66 extends from the angled portion 64 at an angle of, for example, 90 degrees such that a top surface of the extension lip 66 has a substantially horizontal orientation when the liner 50 is oriented as shown in FIG. 6 (i.e., perpendicular to angled portion 64). Such a horizontal orientation of the top surface of the extension lip 66 may be substantially parallel to an orientation of an upper surface of the inside of the groove 34 when the liner 50 is properly seated within the cup 20. However, the present disclosure is not so limited and the angled portion 64 and/or the extension lip 66 can have any orientations with respect to one another and/or with respect to the outer surface 52 of the liner 50 suitable for ensuring the extension lip 66 properly snaps into the groove 34 and secures the liner 50 into the cup 20.

The locking feature 62 can be disposed at any position below the outward-protruding scallops 58. In some aspects, the locking feature 62 is positioned just below (e.g., substantially immediately below and adjacent to) the outward-protruding scallops 58. Accordingly, the locking feature 62 is positioned along the exterior of the liner 50 such that, when it engages with the cup 20, the locking feature 62 is positioned at or below the cylindrical band 26 of the cup 20. In another aspect, the locking feature 62 is located at or around a mid-way point as measured from the liner rim 56 and the liner apex at the distal end of central axis 60.

Turning to FIGS. 8A-8D, which illustrate partial sectional side views of a cup 20 having a poly liner locking feature 62 of the liner 50 engaged with groove 34 of the cup 20. The cup assembly 10 is dimensioned to optimize the amount of capture between the locking feature 62 and groove 34 to ensure proper position, fit, and/or fixation of the liner 50 relative to the cup 20. By optimizing the interference between the liner 50 and cup 20 through tolerances and dimensions of at least the locking feature 62 and the groove 34, the acetabular cup assembly 10 disclosed herein has enhanced characteristics for assembly and resistance to dissociation.

Figure 8A:
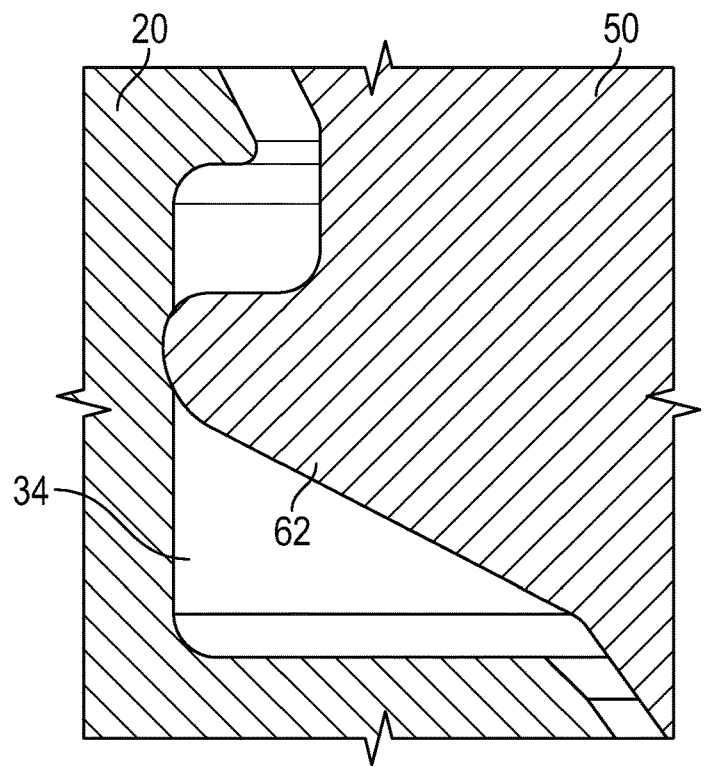
FIG. 8A-8D are cross-sectional views of a locking feature of a liner engaged with a groove of an acetabular cup, according to some embodiments.
Figure 8B:
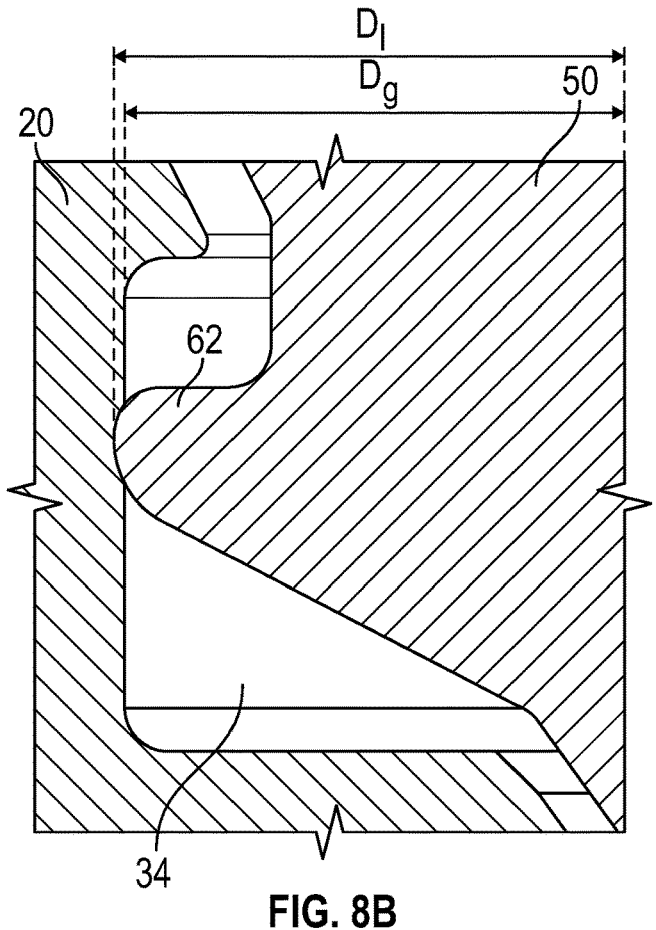

As seen in FIG. 8A, the engagement of the locking feature 62 and cup 20 should have sufficient capture such that the hold is sufficiently strong with the least amount of interference (i.e., relatively low push-in force) and can be assembled with most interference (i.e., removal of the device should require relatively and/or comparatively high push-out force). In some embodiments, as the liner 50 is introduced into the cup 20, locking feature 62 engages the inner surface of the cup 20 and is urged into groove 34. As seen in FIG. 8B, the outside diameter ($D_l$) of the locking feature 62 and inside diameter ($D_g$) of the cup groove 34 are sized to squeeze or very slightly deform the locking feature 62 to optimize liner alignment and stability leading to increased push-out strength. For example, in some embodiments, outside diameter ($D_l$) of the locking feature 62 can be up to about 0.03 inches larger than the inside diameter ($D_g$) of the cup groove 34. In some embodiments, outside diameter ($D_l$) of the locking feature 62 can be up to about 0.008 inches larger than the inside diameter ($D_g$) of the cup groove 34. In some embodiments, outside diameter ($D_l$) of the locking feature 62 can be up to about 0.002 inches smaller than the inside diameter ($D_g$) of the cup groove 34. Accordingly, in some embodiments where $D_l$ is smaller than $D_g$, the squeeze and/or very slight deformation of the locking feature 62 may no longer occur once locking feature 62 has settled into the cup groove 24. In some such embodiments, when the liner 20 is seated in position, the locking feature 62 secures the liner to the cup 20.

Figure 8C:
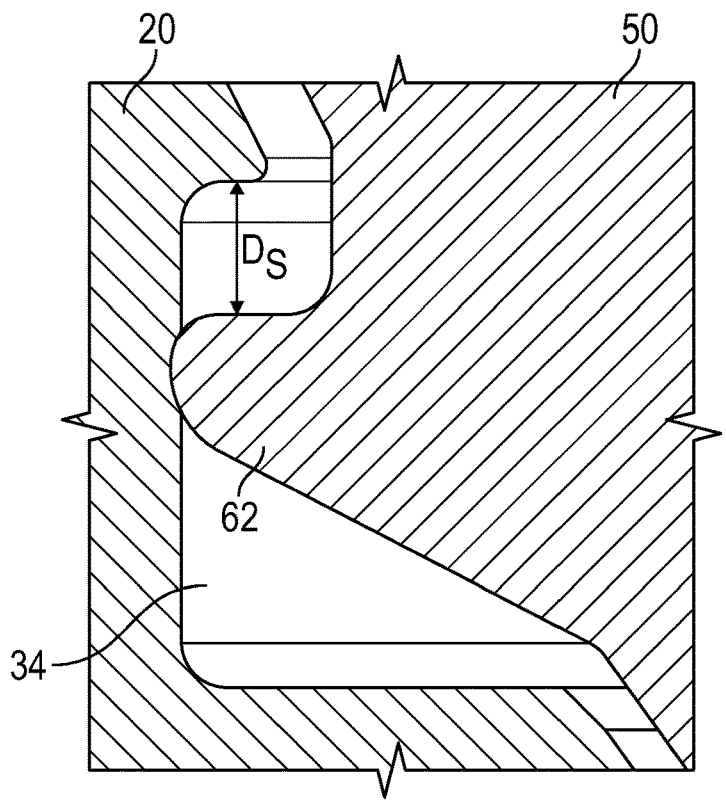
Figure 8D:
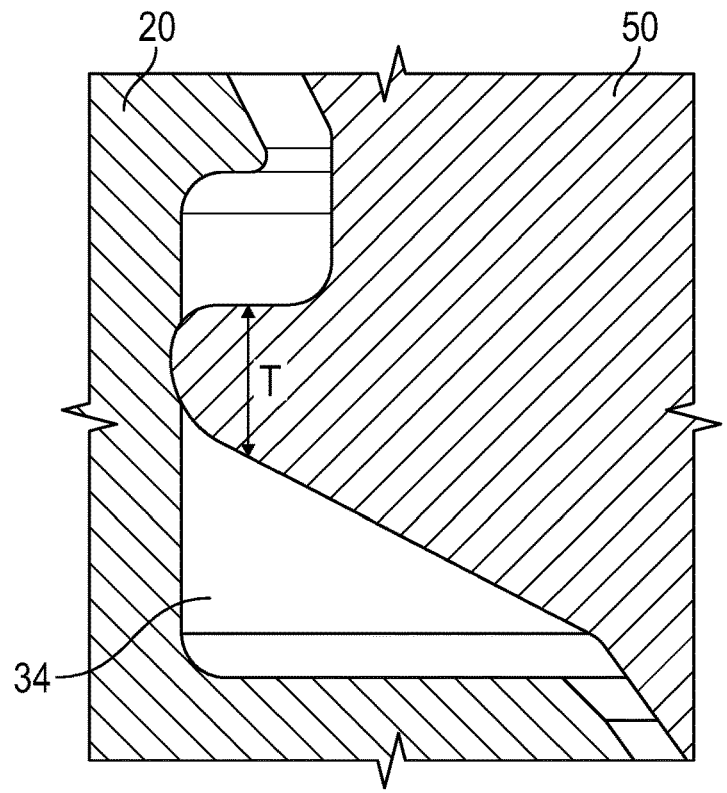
Figure 9:
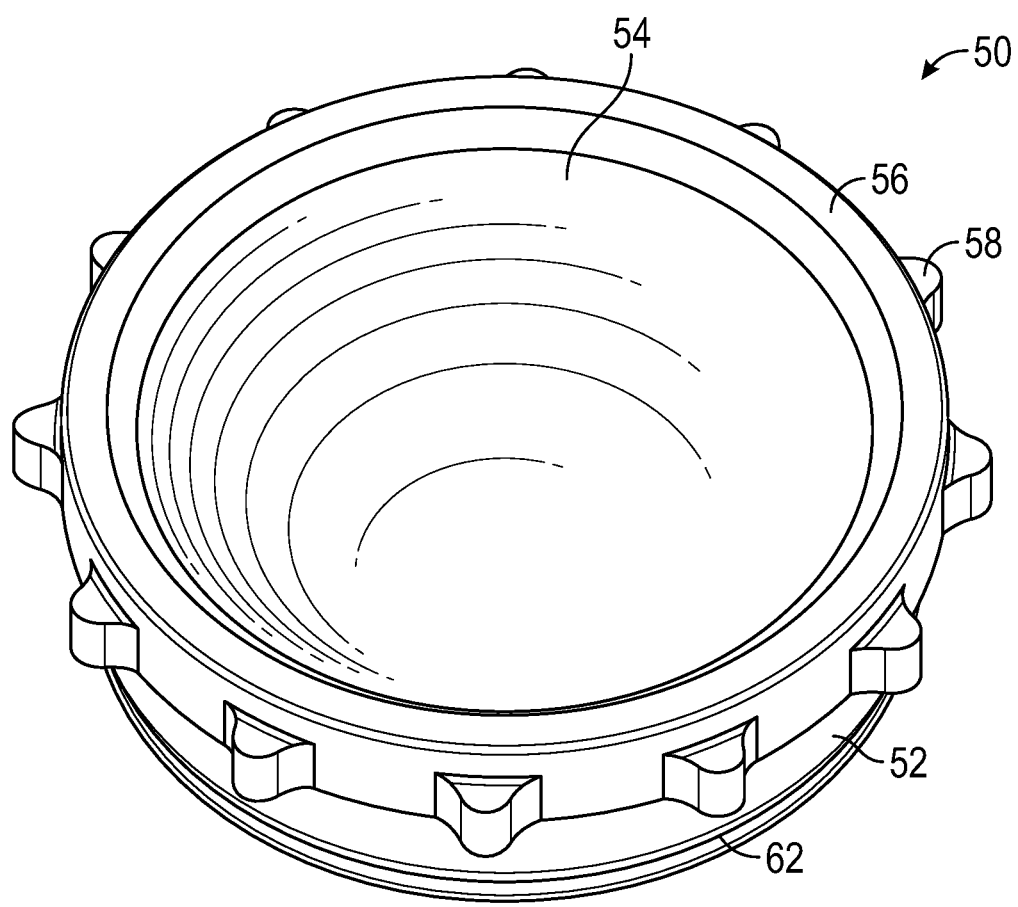
FIG. 9 is a top perspective view of the liner of FIGS. 6-8D, according to some embodiments.

In FIG. 8C, the locking feature 62 is configured to optimize clearance between the top of the locking feature 62 and the top of the groove 34 to ensure that the locking feature 62 has sufficient distance ($D_S$) to spring back into the groove 34 and thereby be fully captured. For example, in some embodiments, distance ($D_S$) is approximately equal to, or slightly greater than, a distance from the angled portion 64 of the locking feature 62 to the outermost tip of the extension lip 66 of the locking feature 62. In FIG. 8D, the locking feature 62 is dimensioned with a shear thickness (T) sufficient to ensure sufficient strength at the thinnest condition. Advantageously, in some embodiments, the shear thickness (T) is 0.02 inches or less. In some embodiments, the shear thickness (T) is greater than or equal to 0.016 inches. However, the present disclosure is not so limited and the shear thickness (T) can have any suitable value. The thickness of the locking feature 62 is selected to ensure adequate strength so that the liner 50 does not push out with too little force to snap into place within the groove 34 while also avoiding being too thick such that full and secure assembly is prevented.

Figure 11:
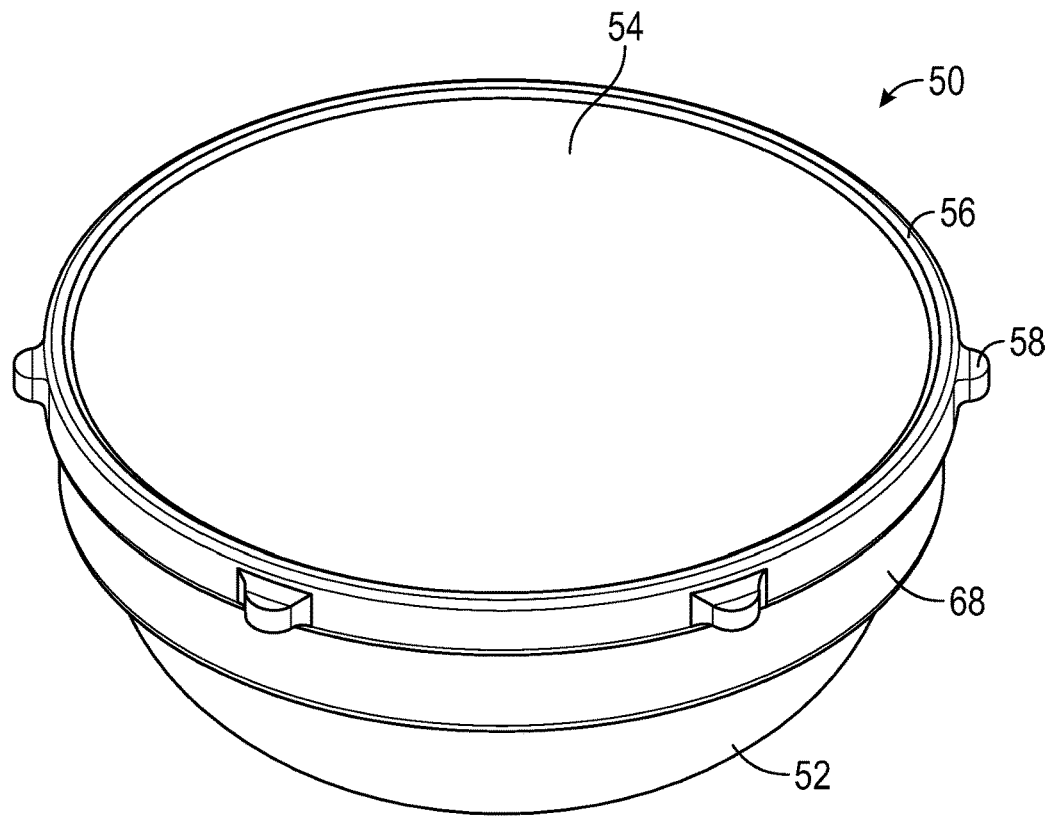
FIG. 11 illustrates a perspective top view of the liner of FIG. 10, according to some embodiments.

Turning to FIGS. 10 and 11, additional embodiments of a liner 50 are illustrated. In some embodiments, the liner 50 is cylindrically symmetric about the central axis 60. However, once installed, rotation of the liner 50 within the cup 20 is prevented and micromotion therebetween is reduced at least partly as a result of interlocking of a plurality of outward-protruding scallops 58 on the liner 50 with the inward-facing protrusions 22 of the cup 20.

The liner 50 is designed to mate with the cup 20. Accordingly, similar to the cup 20, the liner 50 is substantially hemispherical in shape and has a liner outer surface 52, which is substantially convex (as viewed from the outside) and a liner inner surface 54, which is substantially concave (as viewed from the inside).

The liner 50 comprises a liner rim 56 disposed at the top of the liner outer surface 52 and a plurality of outward-protruding scallops 58 which extend from the outer surface 52 of the liner 50 at the rim 56. In one embodiment, the number of outward-protruding scallops 58 is equal to a number of inward-facing recessed scallops 22 of the cup 20. In another embodiment, the number of outward-protruding scallops 58 will be less than the number of inward-facing scallops 22 of the cup 20. For example, in some embodiments, the number of outward-protruding scallops 58 may be half the number (e.g., 6) of inward-facing recessed scallops 22 of the cup 20 (e.g., 12). And in some embodiments, a number of evenly spaced inward-facing recessed scallops 22 of the cup 20 is an integer multiple of a number of evenly outward-protruding scallops 58 on the liner 50 to ensure multiple compatible rotational orientations between the cup 20 and the liner 50.

As described above, these outward-protruding scallops 58 are configured to facilitate the alignment and fixation of the liner 50 with respect to the cup 20 by engaging the inward-facing recessed scallops 22 of the cup 20 and substantially rotationally fixing the liner 50 with respect to the cup 20. In some embodiments, the plurality of outward-protruding scallops 58 have a thickness $t_2$ that is as thin as practical such that liner 50 rests as close as practical to an "engaged" position above the cup 20 when the liner 50 is disposed on a top of the cup 20 but oriented with sufficient axial rotation, relative to an "aligned" position with the cup 20, to initially prevent the plurality of outward-protruding scallops 58 of the liner 50 from interlocking with the plurality of inward-facing scallops 22 of the cup 20 and to initially prevent the liner 50 from entirely seating in the cup 20. This initial orientation between the cup 20 and the liner 50 ensures the liner 50 is properly aligned with the cup 20 in a "pre-installed" position. Deliberately providing the plurality of outward-protruding scallops 58 with a thickness $t_2$ that is as thin as practical provides several benefits over systems having a greater thickness. For example, such a minimal thickness $t_2$ ensures the liner 50 only has to descend a minimal distance from the above-described "pre-installed" position to the "aligned" and "engaged" position, which significantly reduces the probability of liner 50 becoming misaligned when secured to the cup 20.

In some embodiments, at least an upper portion 68 of the outer surface 52 of the liner 50 can be tapered (e.g., an upper portion configured to mate against the upper tapered wall portion 28 of the cup 20). Advantageously, in some such embodiments, the degree of such a taper mirrors the taper of the upper tapered wall portion 28 of cup 20 and, therefore, can have a degree of taper of any angle or range of angles as described above with respect to the upper tapered wall portion 28 of cup 20. In some such embodiments, the tapered upper portion 68 of the outer surface 52 of the liner 50 provides an interference and/or friction fit with the upper tapered wall portion 28 of cup 20. In some such embodiments, liner 50 may not be configured to extend into any annular groove 34 formed in the inner surface 14 of the cup 20. Accordingly, in some such embodiments, liner 50 does not include the locking feature 62 as previously described in connection with FIGS. 6-9. Furthermore, in some but not all such embodiments, the cup 20 can also omit the annular groove 34.

In some embodiments, the liner 50 comprises a peg 70 extending from a bottom of the outer surface 52 of the liner 50. The peg 70 is configured to engage with the aperture 38 of the cup 20 when the liner 50 is properly seated within the cup 20. In some embodiments, the peg 70 is threaded and configured to engage with mating threads within the aperture 38 of the cup 20, thereby securing the liner 50 within the cup 20. In some embodiments, the peg 70 is configured to rest just above the mating aperture 38 of the cup 20 when the liner 50 is resting on the cup 20 in the above-described "pre-installed" position. When the liner 50 is rotated sufficiently to align the outward-protruding scallops 58 of the liner 50 with the plurality of inward-facing scallops 22 of the cup 20, the liner 50 drops the deliberately-shortened distance to the "aligned" and "engaged" position, defined by the deliberately-decreased thickness $t_2$ of the outward-protruding scallops 58 of the liner 50, and the peg 70 of the liner 50 engages with the aperture 38 of the cup 20, thereby preventing misalignment between the liner 50 and the cup 20.

It should be appreciated that the peg 70 disposed at the bottom of the liner 50 and the deliberately-decreased thickness of the outward-protruding scallops 58 of the liner 50 and/or of the inward-facing scallops 22 of the cup 20 function together to properly and accurately "pre-align" the liner 50 with the cup 20 and then maintain alignment as the liner 50 is seated into its final position within the cup 20. By contrast, systems not utilizing such a peg in connection with such a deliberately-decreased thickness of outward-protruding scallops of a liner and/or of inward-facing scallops of a cup risk an increased probability of misalignment between cups and liners in vivo due at least in part to an increased drop distance and increased off-alignment mobility between such a "pre-aligned" position and such an "aligned" and "engaged" position. Such misalignment and canted liners in vivo have been found to significantly increase the risk of corrosion of the implanted parts. Accordingly, systems, liners and/or cups as disclosed herein provide novel and non-obvious improvements over previous systems, liners and/or cups.

Turning to FIG. 12, in some embodiments, upon securing the liner 50 in the cup 20, liner 50 can be configured to receive a femoral assembly 300 therein. In some embodiments, such a femoral assembly 300 can comprise an outer head 330 disposed over and/or around an inner head 320 and a stem trunnion 330 coupled to the inner head 320. The stem trunnion 330 is configured to be secured within a femur of a patient and configured to secure the inner head 320 to the femur of the patient. The inner head 320 is configured to function as a replacement for the natural proximal head of the femur of the patient. The inner head 320 can comprise any suitable material, e.g., metal, metal alloy, etc. In some embodiments, the outer head 330 functions as a sleeve that provides a low-friction interface with the inner surface of the liner 50. The outer head 330 can comprise any suitable material, e.g., polyethylene, metal, metal alloy, etc.

Figure 13:
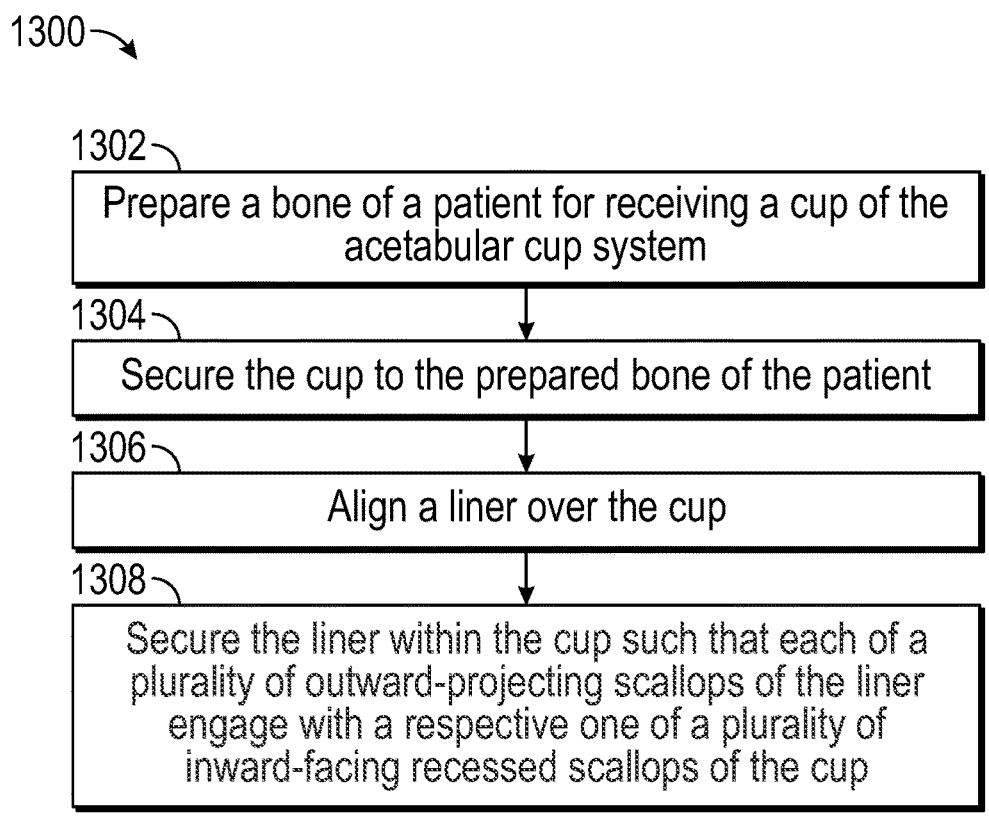
FIG. 13 illustrates a flowchart relating to a method of using an acetabular cup assembly, according to some embodiments.

Discussion now turns to an example method of using an acetabular cup assembly, such as that described in connection with any of FIGS. 1-12. FIG. 13 illustrates a flowchart 1300 corresponding to such a method of use, in accordance with some embodiments. While flowchart 1300 illustrates one or more actions and/or steps, it should be understood that one or more described actions can be omitted, one or more additional or alternative actions can be added, and/or one or more actions can be performed in another order than that specifically described without departing from the spirit or scope of the present disclosure.

Block 1302 includes preparing a bone of a patient for receiving a cup of the acetabular cup system. For example, as previously described in connection with at least one figure, a surgeon can prepare the bone by reaming the acetabular socket to create a surface for accepting the cup 20.

Block 1304 includes securing the cup to the prepared bone of the patient. For example, as previously described in connection with at least one figure, the cup 20 may be held in place by bone cement, an interference or press fit, or one or more bone screws for example, through one or more hole(s) 40 (see, e.g., FIG. 3).

As previously described, the cup 20 comprises an outer surface 16 configured to engage an anatomy, a top face 18 at an upper end of the cup 20, and a generally concave inner surface 14. The generally concave inner surface 14 comprises a cylindrical band 26 having disposed therein a plurality of inward-facing recessed scallops 22 adjacent to the top face 18, a tapered wall 28 disposed adjacent to the cylindrical band 26, and an inner spherical surface 30, 32 adjacent to the tapered wall 28. The inner spherical surface 14 has a substantially uniform radius of curvature and a single groove 34 interrupting the spherical surface 14. In some embodiments, the plurality of inward-facing recessed scallops 22 of the cylindrical band 26 comprises at least twelve inward-facing recessed scallops 22.

In some embodiments, the outer surface 16 of the cup 20 comprises a porous coating configured to aid bone in-growth between the prepared bone of the patient and the outer surface 16 of the cup 20.

Block 1306 includes aligning a liner over the cup. For example, as previously described in connection with at least one figure the surgeon can align the liner 50 over the cup 20. As previously described, the liner 50 can comprise a substantially convex outer surface 52 configured to be received within the concave inner surface 14 of the cup 20, a rim 56 and a plurality of outward-projecting scallops 58 adjacent to the rim 56. In some embodiments, the liner 50 comprises a metallic material. In some embodiments, the metallic material is selected from the group consisting of stainless steel, cobalt-based alloys, a shape memory alloy, tantalum, metal composites, and combinations thereof. In some embodiments, the plurality of outward-protruding scallops 58 comprises at least six outward-protruding scallops 58.

In some embodiments, aligning the liner over the cup (e.g., block 1306) can include aligning a bottom of the peg 70 a predetermined distance $t_2$ above the aperture 38 of the cup 50 when the plurality of outward-protruding scallops 58 of the liner 50 are disposed on the top face 18 of the cup 20 and oriented with sufficient axial rotation relative to the cup 20 to prevent the plurality of outward-protruding scallops 58 of the liner 50 from interlocking with the plurality of inward-facing scallops 22 of the cup 50.

Block 1308 includes securing the liner within the cup such that each of the outward-projecting scallops of the liner engage with a respective one of the inward-facing recessed scallops of the cup. For example, as previously described in connection with at least one figure, in some embodiments (see, e.g., FIGS. 10 ands 11), the outer surface 52 of the liner 50 comprises a tapered portion 68 and securing the liner 50 within the cup 20 comprises engaging the tapered portion 68 of the liner 50 with the tapered wall 28 of the cup 20 in a substantially interference fit. In some embodiments (see, e.g., FIGS. 10 and 11) the cup 20 further comprises an aperture 38 and the liner 50 further comprises a peg 70. In some such embodiments, securing the liner 50 within the cup 20 comprises receiving the peg 70 into the aperture 38.

In some embodiments, securing the liner 50 within the cup 20 comprises axially rotating the liner 50 until the plurality of outward-protruding scallops 58 of the 50 liner interlock with the plurality of inward-facing scallops 22 of the cup 20 and the peg 70 closes the predetermined distance $t_2$ and properly seats within the aperture 38 of the cup 50.

In some embodiments (see, e.g., FIGS. 6-9), the liner 50 comprises polyethylene or another suitable plastic material. In some such embodiments, the liner 50 comprises a locking feature 62 and securing the liner 50 within the cup 20 comprises securing the locking feature 62 within the single groove 34 disposed in the inner spherical surface 14 of the cup 20. In some embodiments, the locking feature 62 has a substantially triangular shape. In some embodiments, the locking feature 62 extends continuously around the outer surface 52 of the liner 50. In some embodiments, the locking feature 62 comprises a plurality of discrete projections disposed discontinuously around the outer surface of the liner 50. In some embodiments, the locking feature 62 comprises an angled portion 64 that has a substantially vertical orientation so as to diverge from the convex outer surface 52 of the liner 50, and an extension lip 66 extending substantially perpendicularly from the angled portion 34 and configured to engage the single groove 34 of the cup 20. In some embodiments, an upper surface of the extension lip 66 has a substantially horizontal orientation that is substantially parallel to an orientation of an upper inside surface of the single groove 34 when the liner 50 is seated within the cup 20. In some embodiments, an outer diameter Dl of the extension lip 66 is greater than an inner diameter $D_g$ of the single groove 34 such that the single groove 34 exerts a deforming force on the extension lip 66 while securing the liner 50 within the cup 20. In some embodiments, a first distance Ds between an upper inside surface of the single groove 34 of the cup 20 and an upper surface of the extension lip 66 of the locking feature 62 is greater than or equal to a second distance from the angled portion 64 to the outermost tip of the extension lip 66 of the locking feature 62.

Reference throughout this disclosure to "an embodiment" or "the embodiment" means that a particular feature, structure or characteristic described in connection with that embodiment is included in at least one embodiment. Thus, the quoted phrases, or variations thereof, as recited throughout this disclosure are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure disclosed herein without departing from the spirit and scope of the disclosure.

What is claimed is:

1. An acetabular cup system, comprising:
a cup configured to receive any one of a plurality of liners, the cup comprising:
an outer surface configured to engage an anatomy,
a top face at an upper end of the cup, and
a generally concave inner surface, comprising:
a cylindrical band having disposed therein a plurality of inward-facing recessed scallops adjacent to the top face,
a tapered wall disposed adjacent to the cylindrical band, and
an inner spherical surface adjacent to the tapered wall, the inner spherical surface having a substantially uniform radius of curvature and a single groove interrupting the spherical surface; and
a liner having a substantially convex outer surface configured to be received within the concave inner surface of the cup, the liner comprising:
a rim,
a plurality of outward-projecting scallops adjacent to the rim, and
a locking feature configured to be secured within the single groove disposed in the inner spherical surface of the cup, the locking feature comprising:
an angled portion that has a substantially vertical orientation so as to diverge from the convex outer surface of the liner, and
an extension lip extending substantially perpendicularly from the angled portion, the extension lip configured to engage the single groove of the cup,
wherein a first distance between an upper inside surface of the single groove of the cup and an upper surface of the extension lip of the locking feature is greater than or equal to a second distance from the angled portion to the outermost tip of the extension lip of the locking feature; and
wherein, when the liner is seated in the cup, each of the outward-projecting scallops of the liner are configured to engage with a respective one of the inward-facing recessed scallops of the cup.

2. The cup system of claim 1, wherein the outer surface of the cup comprises a porous coating.

3. The cup system of claim 1, wherein the liner comprises a metallic material.

4. The cup system of claim 3, wherein the metallic material is selected from the group consisting of stainless steel, cobalt-based alloys, a shape memory alloy, tantalum, metal composites, and combinations thereof.

5. The cup system of claim 1, wherein the outer surface of the liner comprises a tapered portion configured to engage with the tapered wall of the cup when the liner is seated in the cup and thereby retain the liner in the cup.

6. The cup system of claim 1, wherein the plurality of inward-facing recessed scallops of the cylindrical band comprises at least twelve inward-facing recessed scallops.

7. The cup system of claim 1, wherein the plurality of outward-protruding scallops comprises at least six outward-protruding scallops.

8. The cup system of claim 1, wherein the cup further comprises an aperture and the liner further comprises a peg, the aperture being configured to receive the peg and thereby secure the liner to the cup.

9. The cup system of claim 8, wherein a bottom of the peg is configured to be aligned with and suspended a predetermined distance above the aperture of the cup when the plurality of outward-protruding scallops of the liner are disposed on the top face of the cup and oriented with sufficient axial rotation relative to the cup to prevent the plurality of outward-protruding scallops of the liner from interlocking with the plurality of inward-facing scallops of the cup.

10. The cup system of claim 9, wherein the peg is configured to close the predetermined distance and properly seat within the aperture of the cup upon axially rotating the liner until the plurality of outward-protruding scallops of the liner interlock with the plurality of inward-facing scallops of the cup, thereby securing the liner within the cup.

11. The cup system of claim 1, wherein the liner comprises polyethylene.

12. The cup system of claim 1, wherein the locking feature has a substantially triangular shape.

13. The cup system of claim 1, wherein the locking feature extends continuously around the outer surface of the liner.

14. The cup system of claim 1, wherein the locking feature comprises a plurality of discrete projections disposed discontinuously around the outer surface of the liner.

15. The cup system of claim 1, wherein an upper surface of the extension lip has a substantially horizontal orientation that is substantially parallel to an orientation of an upper inside surface of the single groove when the liner is seated within the cup.

16. The cup system of claim 1, wherein an outer diameter of the extension lip is greater than an inner diameter of the single groove such that the single groove exerts a deforming force on the extension lip when the liner is seated within the cup.

17. The cup system of claim 16, wherein the outer diameter of the extension lip is up to 0.03 inches greater than the inner diameter of the single groove.

18. The cup system of claim 1, wherein a thickness of the extension lip is greater than or equal to 0.016 inches.

19. The cup system of claim 1, wherein a thickness of the extension lip is less than or equal to 0.02 inches.

20. A method of using an acetabular cup system, the method comprising:
preparing a bone of a patient for receiving a cup of the acetabular cup system;
securing the cup to the prepared bone of the patient, the cup comprising:
an outer surface configured to engage an anatomy,
a top face at an upper end of the cup, and
a generally concave inner surface, comprising:
a cylindrical band having disposed therein a plurality of inward-facing recessed scallops adjacent to the top face,
a tapered wall disposed adjacent to the cylindrical band, and
an inner spherical surface adjacent to the tapered wall, the inner spherical surface having a substantially uniform radius of curvature and a single groove interrupting the spherical surface;
aligning a liner over the cup, the liner comprising:
a substantially convex outer surface configured to be received within the concave inner surface of the cup,
a rim,
a plurality of outward-projecting scallops adjacent to the rim; and
a locking feature comprising:
an angled portion that has a substantially vertical orientation so as to diverge from the convex outer surface of the liner, and
an extension lip extending substantially perpendicularly from the angled portion, the extension lip configured to engage the single groove of the cup,
wherein a first distance between an upper inside surface of the single groove of the cup and an upper surface of the extension lip of the locking feature is greater than or equal to a second distance from the angled portion to the outermost tip of the extension tip of the extension lip of the locking feature; and
securing the liner within the cup such that each of the outward-projecting scallops of the liner engage with a respective one of the inward-facing recessed scallops of the cup.

21. The method of claim 20, wherein the outer surface of the cup comprises a porous coating configured to aid bone in-growth between the prepared bone of the patient and the outer surface of the cup.

22. The method of claim 20, wherein the liner comprises a metallic material.

23. The method of claim 22, wherein the metallic material is selected from the group consisting of stainless steel, cobalt-based alloys, a shape memory alloy, tantalum, metal composites, and combinations thereof.

24. The method of claim 20, wherein the outer surface of the liner comprises a tapered portion and the securing the liner within the cup comprises engaging the tapered portion of the liner with the tapered wall of the cup in a substantially interference fit.

25. The method of claim 20, wherein the plurality of inward-facing recessed scallops of the cylindrical band comprises at least twelve inward-facing recessed scallops.

26. The method of claim 20, wherein the plurality of outward-protruding scallops comprises at least six outward-protruding scallops.

27. The method of claim 20, wherein the cup further comprises an aperture, the liner further comprises a peg, and the securing the liner within the cup comprises receiving the peg into the aperture.

28. The method of claim 27, the aligning the liner over the cup comprises aligning a bottom of the peg a predetermined distance above the aperture of the cup when the plurality of outward-protruding scallops of the liner are disposed on the top face of the cup and oriented with sufficient axial rotation relative to the cup to prevent the plurality of outward-protruding scallops of the liner from interlocking with the plurality of inward-facing scallops of the cup.

29. The method of claim 28, wherein the securing the liner within the cup comprises axially rotating the liner until the plurality of outward-protruding scallops of the liner interlock with the plurality of inward-facing scallops of the cup and the peg closes the predetermined distance and properly seats within the aperture of the cup.

30. The method of claim 20, wherein the liner comprises polyethylene.

31. The method of claim 20, wherein the securing the liner within the cup comprises securing the locking feature within the single groove disposed in the inner spherical surface of the cup.

32. The method of claim 20, wherein the locking feature has a substantially triangular shape.

33. The method of claim 20, wherein the locking feature extends continuously around the outer surface of the liner.

34. The method of claim 20, wherein the locking feature comprises a plurality of discrete projections disposed discontinuously around the outer surface of the liner.

35. The method of claim 20, wherein an upper surface of the extension lip has a substantially horizontal orientation that is substantially parallel to an orientation of an upper inside surface of the single groove when the liner is seated within the cup.

36. The method of claim 20, wherein an outer diameter of the extension lip is greater than an inner diameter of the single groove such that the single groove exerts a deforming force on the extension lip while securing the liner within the cup.

\* \* \* \* \*